United States Patent
Barrows (12)

(10) Patent No.: US 6,511,748 B1
(45) Date of Patent: Jan. 28, 2003

(54) BIOABSORBABLE FIBERS AND REINFORCED COMPOSITES PRODUCED THEREFROM

(75) Inventor: Thomas H. Barrows, Austell, GA (US)

(73) Assignee: Aderans Research Institute, Inc., Beverly Hills, CA (US)

( * ) Notice: Subject to any disclaimer, the term of this patent is extended or adjusted under 35 U.S.C. 154(b) by 0 days.

(21) Appl. No.: 09/582,833

(22) PCT Filed: Jan. 6, 1999

(86) PCT No.: PCT/US99/00252

§ 371 (c)(1), (2), (4) Date: Jun. 30, 2000

(87) PCT Pub. No.: WO99/34750

PCT Pub. Date: Jul. 15, 1999

Related U.S. Application Data

(60) Provisional application No. 60/070,610, filed on Jan. 6, 1998.

(51) Int. Cl.[7] .................................................. D02G 3/00
(52) U.S. Cl. .................... 428/373; 428/292.1; 428/375; 428/361; 428/374
(58) Field of Search ............................. 428/364, 292.1, 428/373, 374, 375, 361

(56) References Cited

U.S. PATENT DOCUMENTS

| | | | |
|---|---|---|---|
| 4,052,988 A | | 10/1977 | Doddie et al. |
| 4,209,607 A | * | 6/1980 | Shalaby et al. |
| 4,343,931 A | | 8/1982 | Barrows |
| 5,133,739 A | * | 7/1992 | Bezwada et al. |
| 5,147,400 A | * | 9/1992 | Kaplan et al. |
| 5,198,507 A | * | 3/1993 | Kohn et al. |
| 5,403,347 A | | 4/1995 | Roby et al. |
| 5,522,841 A | | 6/1996 | Roby et al. |

* cited by examiner

*Primary Examiner*—Merrick Dixon
(74) *Attorney, Agent, or Firm*—Michael Best & Friedrich LLP; Grady J. Frenchick, Esq.; Charlene L. Yager, Esq.

(57) ABSTRACT

This invention relates to bioabsorbable fibers, comprising a semicrystalline fiber-forming core polymer and an amorphous sheath polymer, wherein the core polymer and sheath polymer are separately melt extruded and connected to one another through an adhesive bond. The present invention also relates to reinforced composites of the bioabsorbable fibers, and to devices comprising the reinforced composites. The devices are suitable for in vivo implantation. Some embodiments of the present devices can also support high loads, making then useful for fracture fixation and spinal fusion. The invention also relates to methods of making the various materials of the invention.

7 Claims, No Drawings

BIOABSORBABLE FIBERS AND REINFORCED COMPOSITES PRODUCED THEREFROM

CROSS-REFERENCE TO RELATED APPLICATIONS

This application claims the benefit of U.S. Provisional Application No. 60/070,610, filed Jan. 6, 1998.

STATEMENT REGARDING FEDERALLY SPONSORED RESEARCH OR DEVELOPMENT

Not Applicable

FIELD OF THE INVENTION

This invention relates to synthetic bioabsorbable fibers. The present invention also relates to methods of making bioabsorbable fibers from at least two different polymers by separately melt extruding the at least two different polymers and bonding the extruded polymers together to form a fiber with a semicrystalline polymer core and an amorphous polymer sheath. The invention also relates to reinforced composites, made at least in part from synthetic bioabsorbable fibers. Finally, the present invention relates to devices comprised of such reinforced composites, wherein the devices are designed for use as in vivo implants, including implants which can support high loads, such as for use in fracture fixation and spinal fusion.

BACKGROUND OF THE INVENTION

Metal implants have a long history of successful use in orthopedic surgery but also carry many risks for complications. In the case of metal rods and plates for fracture fixation, a second surgery for device removal is recommended about one year after confirmation of osseous union. If the device is not removed the bone can remodel into a weakened condition due to stress shielding. There is also the potential for an increased risk of infection. In the case of metal cages for spinal fusion, complications due to migration, infection, corrosion, reduced bone density, non-union, and fracture are especially serious since major surgery is required for device removal.

Poly(lactic acid) has been the subject of continuous research as a material for use in surgical devices since it was first proposed for this purpose in the mid 1960s. Since poly(lactic acid) is ultimately hydrolyzed into lactic acid, a normal intermediate carbohydrate metabolism in man, it continues to be viewed as the ideal implantable material from the standpoint of toxicological safety.

High strength and high modulus fibers produced from semicrystalline poly(L-lactic acid), also known as poly (lactide), hereinafter referred to as PLA, have been studied as braided implants for use as a ligament augmentation device. PLA fibers are known to be capable of retaining about 70% of their initial tensile strength after 10 months in vivo.

In spite of the excellent strength retention of PLA fibers in vivo, molded articles made from PLA have generally failed to achieve commercial success as orthopedic implants. The physical properties of a polymer in fiber form resulting from optimum drawing and annealing of the fiber cannot be duplicated in the same polymer processed by injection molding. Thus injection molded PLA typically may have a tensile strength of 60 MPa. This value may be increased up to about 300 MPa by stressing the injection molded parts to achieve orientation prior to crystallization. Highly drawn PLA fibers, on the other hand, can give tensile strength in excess of 2,000 MPa.

One possibility for obtaining fiber strength in a molded part would be to incorporate PLA fibers into a matrix of PLA or a similar polymer such as poly(dl-lacitc acid) which is totally amorphous. The problem with using poly(dl-lacitc acid) is that it degrades too rapidly for orthopedic applications. Pure self-reinforced PLA fiber composites have been made by sintering together bundles of PLA fibers thereby sacrificing some of the fibers to produce a molten matrix for embedding the remaining fibers. This process is difficult to control and yields unreliable results. It also tends to produce a substantial amorphous phase that can slowly recrystallize upon prolonged storage to give a brittle, non-reinforcing structure. Moreover, even if recrystallization is suppressed by copolymerization of L-lactide with small amounts of dl-lactide, degradation of the amorphous PLA tends to result in the build-up of acidic degradation products in the interior of the molded device resulting in an autocatalytic acceleration of the hydrolytic degradation process.

Fiber reinforced composites of PLA with the use of other bioabsorbable polymers as a matrix have generally failed to achieve adequate in vivo performance due to moisture penetration into the interface between fiber and matrix. This typical mode of failure has been the principal problem with all approaches to fully bioabsorbable composites of the prior art.

BRIEF SUMMARY OF THE INVENTION

In one aspect, the present invention is a bioabsorbable fiber comprising a core of a semicrystalline fiber-forming bioabsorbable core polymer with a crystalline core melting temperature, and a sheath of an amorphous bioabsorbable sheath polymer with a softening point below the crystalline core melting temperature, wherein the core polymer and sheath polymer are separately melt extruded, and the sheath is connected to the core through an adhesive bond.

In another aspect, the present invention is a reinforced composite, comprising a plurality of filaments of the bioabsorbable fiber and a molding resin reinforced therewith.

In yet another aspect, the present invention is a device designed for in vivo implantation or insertion, fabricated from the reinforced composite.

In a further aspect, the present invention is a method of making the bioabsorbable fiber, comprising the steps of:
  a. selecting a core polymer which is semicrystalline, fiber-forming, and bioabsorbable, with a crystalline core melting temperature;
  b. selecting a sheath polymer which is bioabsorbable, and which forms an amorphous phase on polymerization, with a softening point below the crystalline core melting temperature;
  c. separately melt extruding the core polymer and sheath polymer; and
  d. forming an adhesive bond between the core polymer and sheath polymer, such that the resulting bioabsorbable fiber comprises a core of the core polymer and a sheath of the sheath polymer.

Finally, in yet another aspect, the present invention is a method of making a surgical device of a reinforced composite of bioabsorbable fibers, comprising the steps of:
  a. providing a plurality of the bioabsorbable fibers;
  b. providing an injection mold having interior walls which define an interior cavity;
  c. inserting the plurality of bioabsorbable fibers into the interior cavity of the injection mold; and d. adding a bioabsorbable injection molding resin polymer to the injection mold at an injection temperature which is lower than the crystalline core melting temperature.

DETAILED DESCRIPTION OF THE INVENTION

A. Definitions

The following terms used herein shall have the following definitions:

"Poly(ester-amide)" shall mean to include any of the polymers described in U.S. Pat. No. 4,343,931, "Synthetic Absorbable Surgical Devices of Poly(esteramides)", T. H. Barrows, Aug. 19, 1982, the teachings of which are incorporated herein by reference, and to include any of the polymers described in Provisional Patent Application Ser. No. 60/062,064, "Bioabsorbable Triglycolic Acid Poly (ester-amide)s", T. H. Barrows, filed Oct. 16, 1997, the teachings of which are incorporated herein by reference.

"Tryosine-derived polycarbonates" shall mean to include any of the polymers described in U.S. Pat. No. 5,198,507, "Synthesis of Amino Acid-derived Bioerodible Polymers", J. B. Kohn and S. K. K. Pulapura, Mar. 30, 1993, the teachings of which are incorporated herein by reference.

"PLA" shall mean poly(L-lactide).

"PGA" shall mean polyglycolide.

"PEA" shall mean poly(ester-amide).

"TMC" shall mean trimethylene carbonate.

"Softening point" shall mean the temperature range below which a polymer is non-tacky and non-self-adherent and above which the polymer is tacky and self-adherent.

"Melting temperature" shall mean the crystalline core melting transition temperature (Tm) of a semi-crystalline polymer.

"Injection temperature" shall mean the minimum temperature of a molten polymer that allows it to have adequately low viscosity under pressure to flow into an injection mold cavity containing multifilament fibers such that the spaces between the fibers are completely filled with the injected molten polymer.

"Bioabsorbable" shall mean the property of a composition, material, or device, that allows it to degrade post-implantation completely into non-toxic degradation products that are eliminated from the body or are transformed into normal metabolites utilized within the body.

B. Bioabsorbable Fibers

The present invention provides fibers fabricated by a core-sheath coextrusion process in which two different bioabsorbable polymers are separately melt extruded and forced into a single die such that the resultant filaments are comprised of one polymer substantially at the core and the other polymer substantially as a sheath. The core polymer is preferably a semicrystalline, high strength fiber-forming polymer and the sheath polymer is preferably a normally amorphous polymer with a softening point well below the crystalline melting temperature of the core polymer (hereinafter, the "crystalline core melting temperature"). The sheath polymer also preferably has a softening point high enough that it is tack-free at the temperatures required for optimum hot drawing and annealing of the core fiber.

The two polymers must be capable of forming an adequate adhesive bond between them such that when the molten filament is solidified by cooling and subsequently hot stretched, the sheath polymer will elongate with the core polymer and not separate from the core. The coextrusion process in which the two polymers come into contact with each other in the molten phase provides the optimum environment needed for the development of an interfacial bond that will tolerate said processing without failure. Thus an important feature of the present invention is the discovery that dissimilar bioabsorbable polymers that normally would not adhere to each other by hot pressing the two polymers as pre-formed solid articles adhere well as a result of an intimate interface created during coextrusion.

A further advantage of the present invention is that sheath polymers can be selected from a wide variety of known bioabsorbable polymers as well as from custom formulated blends and or custom synthesized copolymers. Sheath polymers are preferably selected which have a softening point value which ensures subsequent processing of the core component filaments to produce high strength fibers. Sheath polymers are also preferably selected to optimize the integrity of adhesion between the sheath and the core, by minimizing the penetration of moisture into the interface between the sheath and core, and by ensuring moisture penetration into the interface between the sheath and core does not occur at a rate faster than moisture penetration into the bulk of the sheath polymer.

Said fibers ideally are fine multifilaments since it is known in the art of fiber spinning that maximum draw ratio and therefore maximum tensile strength and modulus are achieved more readily with small rather than large diameter fibers. In addition, multifilament yarns are more versatile in subsequent device fabrication processing steps than monofilament fiber.

Fibers of the present invention are comprised of a core of one bioabsorbable polymer, the "core polymer", and a partial or complete sheath of a second bioabsorbable polymer, the "sheath polymer". The core polymer is preferably selected from the group consisting of poly(L-lactide), polyglycolide, poly(epsilon-caprolactone), polydioxanone, poly(ester-amide)s, and any combination of copolymers of said polymers including copolymers made with the use of trimethylene carbonate and or dl-lactide as comonomers. The sheath polymer is preferably selected from the group consisting of poly(ester-amide)s, tyrosine-derived polycarbonates, poly(trimethylene carbonate), poly(dl-lactide), polydioxanone, poly(epsilon-caprolactone), and copolymers, mixtures, and blends of these polymers. Alternatively, the sheath polymer is the product of copolymerization of any two or more monomers selected from the group comprised of epsilon-caprolactone, trimethylene carbonate, L-lactide, dl-lactide, glycolide, and para-dioxanone.

The specific core and sheath polymers suitable for inclusion in a given biocomponent fiber of the present invention depends upon the intended use for the particular biocomponent fiber. For example, if the fiber is to be used to fabricated a device for implantation into bone, the preferred core polymer is PLA and the preferred sheath polymer is selected from the group comprised of polyTMC, poly(TMC-co-L-lactide), poly(TMC-co-epsilon-caprolactone), tyrosine-derived polycarbonates, and PEAs.

The preferred core polymer for fracture fixation and spinal fusion devices is PLA due to its high strength, stiffness, and long-lasting strength retention. The slow degradation time of crystalline PLA fibers is not anticipated to result in the release of excessively acidic degradation products due to the long time course of degradation. The sheath polymer and the molding resin polymer, on the other hand, preferably are not PLA or PLA/PGA copolymers since the release of acidic degradation products and the autocatalytic acceleration of the degradation process mentioned previously are possible drawbacks. Instead, polycarbonates such as polyTMC, polyTMC copolymers, and tyrosine-derived polycarbonates as well as certain PEAs are preferred since they degrade slowly, are relatively hydrophobic, and do not release a significant amount of acidic degradation products.

Triglycolic acid PEAs are especially preferred as sheath polymers and as molding resin polymers since they provide exceptionally good inter-fiber adhesion due to their "hot melt" adhesive properties. A further advantage of triglycolic acid PEAs is that they can be block copolymerized with PLA to provide a strong intermolecular interaction with the molten PLA core during coextrusion and thus provide an interfacial bond between core and sheath that is highly resistant to premature moisture penetration. Similarly, TMC can be randomly or block copolymerized with lactide or caprolactone both to increase the softening point of pure polyTMC and to improve its compatibility as a sheath polymer with the PLA core during the coextrusion process. Pure polyTMC of an appropriate molecular weight may be a suitable injection molding resin polymer due to its low injection temperature, slow degradation rate, hydrophobic nature, and non-acidic degradation products.

C. Production of Reinforced Composites

The biocomponent fibers of the present invention can be processed into reinforced composites by a number of different methods. A preferred method is injection molding. Thus short (e.g. 1–10 mm) chopped fibers can be added to a molding resin polymer such that the "filled" molding resin contains about 10 to 70% of reinforcement fibers by volume.

Alternatively the injection molding cavity can be pre-loaded with a fabric of said fibers in continuous form and injected with an injection molding resin polymer selected from any of the polymers in the group identified above as sheath polymers. The injection molding resin polymer may be the same polymer as the sheath polymer of the continuous fibers or a different polymer. Optionally, the injection molding resin polymer also may be "filled" with a reinforcement filler in the form of short fibers of the present invention and or a mineral filler such as hydroxyapatite. Mineral fillers also optionally may be pre-treated with coupling reagents such as silane coupling agents known in the prior art to provide improved bonding to injection molding resin polymers.

D. Production of Devices of the Reinforced Composites

Production of devices of the reinforced composites of the present invention can be achieved most conveniently by injection molding with a molding resin that is "filled" with the above fibers cut into short lengths. The molding resin can be the same polymer as the sheath polymer or a polymer of similar composition such that excellent adhesion is obtained between the molding resin and the sheath of the reinforcing fiber. The injection temperature of the molding resin may be higher or lower than the softening temperature of the sheath polymer, but must be below the melting temperature of the core polymer.

An especially advantageous use for the bioabsorbable fibers of the present invention is in the fabrication of high strength tubular implants for use as intramedullary rods for fracture fixation and as cage implants for spinal fusion. Thus the biocomponent fibers are first tightly wrapped around a mandrel in multiple layers with a ply angle of about 45 degrees. The fiber covered mandrel then serves as the core of an injection mold cavity which is injected with the appropriate bioabsorbable polymer to obtain a solid, fiber reinforced tubular device. The bending strength of the tubular device is determined by the wall thickness which can be varied by varying the diameter of the mandrel or the dimensions of the injection molding cavity. The external surface of the device can be provided with any desired texture or added features such as parallel flutes for implant stabilization by proper design of the mold cavity.

Similarly, a threaded, perforated, spinal fusion cage can be fabricated by inserting retractable pins into the mandrel core of the mold cavity and winding fibers at a lower ply angle (e.g. about 30 degrees) such that the fibers are aligned more closely with the axis of the mandrel and are woven between the pins. The pins serve both to prevent the fibers from shifting during injection molding and to provide perforations in the device needed for autologous bone graft placed by the surgeon in the "cage" to grow out into the surrounding space. Alternatively, a loosely woven fabric of the biocomponent fibers can be wrapped many times around the mandrel with protruding removable pins such that the fibers separate enough to allow the pins to pass through the fabric. In this way most of the fibers can be aligned completely parallel with the axis of the mandrel which is the direction in greatest need of reinforcement if the device is implanted parallel to the spinal column. Upon clamping the mold and injecting it with the appropriate bioabsorbable polymer molding resin, cooling, parting the mold, extracting the pins, and retracting the mandrel core, the finished part will be a solid fiber reinforced tube with perforations in the wall corresponding to the number and size of the pins. The external surface of the device can be provided with any desired texture or added features such as threads for implant stabilization by proper design of the mold cavity.

The molding resin optionally can be modified by the addition of other additives such as finely divided mineral such as hydroxyapatite to improve the hardness of the molding resin. This could be especially useful in the case of the threaded spinal fusion cage since the mineral would tend to be filtered out of the fiber containing portion of the mold and concentrated in the open cavities that form the threads where it is most needed. PEA is an especially preferred molding resin for use with a mineral filler since the nylon like character of PEA ensures good adhesion of the polymer to the filler if a silane coupling agent such as trimethoxyaminopropyl silane is used to pre-treat the mineral filler.

The spinal fusion devices of the present invention, produced as described above, function in a manner similar to commercially available titanium fusion cages. These cages are packed with autologous bone chips which eventually regenerate new bone that grows through the holes in the cylinder walls as well as through the open ends of the tube thereby bridging or "fusing" the adjacent vertebral bodies. A superior long term result is anticipated with fully bioabsorbable devices of the present invention since the implant gradually transfers loads onto the new bone thereby stimulating it to remodel into denser, more functional tissue. Ultimately the fully bioabsorbable device of the present invention will be completely replaced with new bone that can remodel into normal healthy tissue.

Other thinner more flexible tubular devices such as stents can be produced from fibers of the present invention by placing woven, nonwoven, knitted, or braided fabric or mesh around a mandrel and injection molding. Upon cooling and removing the mandrel, a tubular stent with the desired degree of stiffness and porosity (imparted by the surface topography of the mold cavity or mandrel core) will be obtained. Such stents are useful in a variety of surgical applications such as in the urinary tract, bile duct, and peripheral nerves. The fibrous nature of the composite ensures good suture holding strength in thin walled constructions.

Other methods of processing fibers of the present invention into composite structures and other uses for such composite materials will be apparent to those skilled in the art of fiber processing and surgical device fabrication.

EXAMPLES

The following examples are given to illustrate various aspects of the invention, without limiting the scope thereof:

Example 1

Bicomponent Fiber of PLA Core and poly(TMC-co-L-lactide) Sheath

A copolymer of TMC and L-lactide is prepared from a mixture of L-lactide and TMC by heating under an inert atmosphere and anhydrous conditions with stirring in the presence of stannous octoate as a catalyst and lauryl alcohol as an initiator. The ratio of L-Iactide to TMC is adjusted so that the resulting high molecular weight polymer has a softening point below the crystalline melting point of PLA (e.g. about 180° C.) and above the temperature needed to hot stretch and anneal PLA fibers (e.g. about 90–110° C.).

PLA and the above poly(TMC-co-L-lactide) polymers are separately melt extruded into a single specially designed multifilament core-sheath spinneret. The ratios of polymers are adjusted such that the core is 60–90% by volume and the sheath is 40–10% by volume. After maximum drawing, the fiber tow is annealed to give high tensile strength, high modulus fibers that are in the size range of 3–20 denier per filament.

Example 2

Bicomponent Fiber of PLA Core and poly(TMC-co-epsilon-caprolactone) Sheath

A core-sheath polymer fiber is produced as described in Example 1 except that TMC and epsilon-caprolactone are copolymerized in the appropriate ratio to obtain a sheath polymer with the proper softening point for use in coextrusion with PLA.

Example 3

Bicomponent Fiber of PLA Core and poly(TMC-co-para-dioxanone) Sheath

A core-sheath polymer fiber is produced as described in Example 1 except that TMC and para-dioxanone are copolymerized in the appropriate ratio to obtain a sheath polymer with the proper softening point for use in coextrusion with PLA.

Example 4

Bicomponent Fiber of PLA Core and PEA Sheath

A core-sheath polymer fiber is produced as described in Example 1 except that poly[2,5-dioxahexane-1,6-di (carbonyloxy)hexane-1,6-di (amidocarbonylpentamethylene)], prepared as described in Provisional Patent Application by T. H. Barrows entitled, "Bioabsorbable Triglycolic Acid Poly(ester-amide)s", filed Oct. 16, 1997, is used for coextrusion with PLA.

Example 5

Bicomponent Fiber of PLA Core and PEA-co-block-PLA Sheath

A core-sheath polymer fiber is produced as described in Example 4 except that the sheath polymer is further reacted with L-lactide to form a block copolymer. This block copolymer is described in Provisional Patent Application by T. H. Barrows entitled, "Bioabsorbable Triglycolic Acid Poly(ester-amide)s", filed Oct. 16, 1997. This sheath polymer is used for coextrusion with PLA.

Example 6

Bicomponent Fiber of PLA Core and Tyrosine-derived Polycarbonate Sheath

A core-sheath polymer fiber is produced as described in Example 1 except that poly(DTH carbonate) prepared as described in U.S. Pat. No. 5,198,507 is used for coextrusion with PLA.

Examples 7 through 12

Bicomponent Fibers of PGA Core

The bicomponent fibers of Examples 1 through 6, respectively, are produced in a similar manner except that PGA is used instead of PLA as the core polymer. The sheath polymers in Examples 7 and 11 are copolymers made with the substitution of glycolide for lactide.

Example 13

Bicomponent Fibers of PGA Core and poly(dl-lactide) Sheath

The bicomponent fibers of Example 1 are produced in a similar manner except that PGA is used instead of PLA as the core polymer and poly(dl-lactide) is used as the sheath polymer.

Example 14

Bioabsorbable Biocomponent Fiber Reinforced Injection Molding Resins

Biocomponent fibers prepared as described in any of the above Examples 1–13 are cut into 1–3 mm lengths and melt blended with 30 to 90% by volume of the corresponding sheath polymer and extruded at a temperature below the melting temperature of the core polymer into a 3–6 mm diameter strand, cooled, and cut into pellets with a cutting machine to produce pelletized fiber filled resin for injection molding.

Example 15

Bioabsorbable Biocomponent Fiber Reinforced Insert Injection Molded Spinal Fusion Cage A loosely woven or knitted fabric in the form of a 3 cm wide continuous strip is produced from any of the fibers in Examples 1 through 6. This fabric is wound around a mandrel that is 7 mm in diameter and features an equally spaced array of 24 protruding 3 mm diameter pins over a central 3 cm length such that the open spaces in the fabric allow the pins to pass through the fabric. The fabric is then tightly wound on the surface of the mandrel to build up a 4 mm thick layer of fabric. The mandrel thus prepared is inserted into a specially design injection molding cavity that both mates with the pins and has an inner surface that produces an outer surface for the resultant molded part that features 1 by 3 mm threads.

With the mold properly clamped it is then injected with molten polymer that has approximately the same composition as the sheath polymer in the reinforcement fibers. The injection molding resin polymer preferably has a low injection temperature and low viscosity to ensure complete impregnation of the reinforcement fabric. Upon completion of the molding cycle, the mold is parted, the pins are extracted, and the part is ejected by retraction of the core. The resultant injection molded part is an open tube approximately 3 cm long and approximately 15 mm in diameter with threads on the external surface and 24 equally spaced 3 mm diameter holes passing through the wall of the tube.

The bioabsorbable fiber reinforced spinal fusion cage described above can be utilized to bridge and fuse adjacent vertebrae in the same manner as commercially available titanium fusion cages. Thus two such cages are filled with autologous bone chips and threaded into separate predrilled and tapped holes created in the surfaces of the adjacent vertebrae facing the space created by removal of the disc. Unlike the metal implants, however, the fusion cage of this example is fully bioabsorbable. Thus over time after the graft of bone chips "takes" and heals, the implant slowly weakens due to degradation and gradually transfers mechanical loads onto the new bone, thereby stimulating it to remodel into a stronger, denser, more functional tissue than is possible for a bone graft confined in a metal implant. Ultimately the fusion cage of this example is bioabsorbed and eliminated from the body, thereby creating additional space for the regeneration of more new bone.

Example 16

Bioabsorbable Biocomponent Fiber Reinforced Insert Injection Molded Spinal Fusion Cage Containing Hydroxyapatite Reinforcement Filler The bioabsorbable fusion cage of Example 15 is produced in a similar manner except that the injection molding resin is "filled" with 10 to 70% by volume of hydroxyapatite mineral in finely divided form, preferably surface treated with a coupling agent such as trimethoxyaminopropyl silane to promote adhesion of the mineral filler with the injection molding resin polymer. This filler provides a device with greater hardness and strength. It also reduces the volume of bioabsorbable polymer in the implant and replaces it with a mineral that is normally present in bone and will be incorporated into the new bone that is formed upon bioabsorption of the implant. Although the fabric may act as a filter and prevent filler from entering the spaces between the fibers, this would result in the filler being concentrated in the threads of the device where would be most useful.

Example 17

Bioabsorbable Biocomponent Fiber Reinforced Insert Injection Molded Tubular Stent A PGA core biocomponent fiber selected from those described in Examples 7 through 13 is used to fabricate a knitted or woven fabric. The fabric is wrapped around a mandrel that forms the core of an injection molding cavity. The mold is then injected with molten polymer selected for any of the above mentioned sheath polymers. Upon cooling, parting the mold, and retracting the core, a thin walled, semi-rigid tube with good suture holding properties is formed that can be used as a stent for peripheral nerve grafting, bile duct reconstruction, and in ureter and urethra reconstruction.

What is claimed is:

1. A bioabsorbable fiber comprising a core of a semicrystalline fiber-forming bioabsorbable core polymer with a crystalline core melting temperature, and a sheath of an amorphous bioabsorbable sheath polymer with a softening point below the crystalline core melting temperature, wherein the core polymer and sheath polymer are separately melt extruded, and die sheath is connected to the core through an adhesive bond.

2. The bioabsorbable fiber of claim 1, wherein the core polymer is selected from the group consisting of poly(L-lactide), polyglycolide, poly(epsilon-caprolactone), polydioxanone, poly(ester-amide)s, any combination thereof, and any copolymers thereof wherein trimethylene carbonate is a comonomer.

3. The bioabsorbable fiber of claim 1, wherein the sheath polymer comprises at least one polymer selected from the group consisting of poly(ester-amide)s, tyrosine-derived polycarbonates, poly(trimethylene carbonate), poly(dl-lactide), polydioxanone, and any copolymer, mixture, or blend thereof.

4. The bioabsorbable fiber of claim 1, wherein the sheath polymer comprises a copolymer which is the product of copolymerization of at least two monomers selected from the group of monomers consisting of epsilon-caprolactone, trimethylene carbonate, L-lactide, dl-lactide, glycolide, and para-dioxanone.

5. The bioabsorbable fiber of claim 1, wherein the core polymer is poly(L-lactide) and the sheath polymer is a block copolymer of poly(ester-amide) and L-lactide.

6. The bioabsorbable fiber of claim 5, wherein the sheath polymer is a block copolymer of L-lactide and 1,6-hexanediol terminated poly[2,5-dioxahexane-1,6-di(carbonyloxy)hexane-1,6-di(amidocarbonylpentamethylene)].

7. The bioabsorbable fiber of claim 1, wherein the sheath is bound to the core with sufficient strength that the sheath elongates with the core and does not separate therefrom through hot stretching, elongation, and cooling of the fiber.

* * * * *